(12) United States Patent
Kim et al.

(10) Patent No.: US 7,611,878 B2
(45) Date of Patent: *Nov. 3, 2009

(54) BIOCATALYTIC MATERIAL COMPRISING MULTILAYER ENZYME COATED FIBER

(75) Inventors: Jungbae Kim, Richland, WA (US); Ja Hun Kwak, Richland, WA (US); Jay W. Grate, West Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 324 days.

This patent is subject to a terminal disclaimer.

(21) Appl. No.: 11/251,540

(22) Filed: Sep. 30, 2005

(65) Prior Publication Data

US 2007/0077567 A1 Apr. 5, 2007

(51) Int. Cl.
C12N 11/00 (2006.01)
C12N 11/14 (2006.01)
C12N 11/02 (2006.01)
C12N 11/08 (2006.01)

(52) U.S. Cl. .................. 435/174; 435/176; 435/177; 435/180

(58) Field of Classification Search ...................... None
See application file for complete search history.

(56) References Cited

U.S. PATENT DOCUMENTS

| 4,665,028 A | 5/1987 | Amotz |
| 2004/0121018 A1 | 6/2004 | Grate et al. |
| 2007/0077565 A1 | 4/2007 | Kim et al. |
| 2007/0077566 A1 | 4/2007 | Kim et al. |
| 2007/0077568 A1 | 4/2007 | Kim et al. |

FOREIGN PATENT DOCUMENTS

WO 03106655 12/2003

OTHER PUBLICATIONS

Bode et al., "Crude Aminoacylase From *Aspergillus* sp. Is a Mixture of Hydrolases," Biotechnol. Bioeng. 84:710-713, 2003.
Cabriol et al., "Immobilized Hydroxynitrile Lyases for Enantioselective Synthesis of Cyanohydrins: Sol-Gels and Cross-Linked Enzyme Aggregates," *Adv. Synth. Catal.* 348:1645-1654, 2006.
Cao et al., "Cross-Linked Enzyme Aggregates: A Simple and Effective Method for the Immobilization of Penicillin Acylase," *Organic Letters* 2(10):1361-1364, 2000.
Cao et al., "Cross-linked aggregates of penicillin acylase: robust catalysts for the synthesis of β-lactam antibiotics," *Journal of Molecular Catalysis* 11:665-670, 2001.
Cao et al., "Immobilised enzymes: carrier-bound or carrier-free?," *Current Opinion in Biotechnology* 14:387-394, 2003.
Chmura et al., "Cross-Linked Aggregates of the Hydroxynitrile Lyase from *Manihot esculenta*: Highly Active and Robust Biocatalysts," *Adv. Synth. Catal.* 348:1655-1661, 2006.
Fischback et al., "Miniature Biofuel Cells with Improved Stability Under Continuous Operation," *Electroanalysis* 18(19-20):2016-2022, 2006.
Hobbs et al., "Continuous kinetic resolution catalysed by cross-linked enzyme aggregates, 'CLEAs', in Supercritical $CO_2$," *Green Chem.* 8:816-821, 2006.

Kim et al., "Preparation of biocatalytic nanofibres with high active and stability via enzyme aggregate coating on polymer nanofibres," *Nanotechnology* 16:S382-388, 2005.
López-Serrano et al., "Cross-linked enzyme aggregates with enhanced activity: application to lipases," *Biotechnology Letters* 24:1379-1383, 2002.
Mateo et al., "A New, Mild Cross-linking Methodology to Prepare Cross-Linked Enzyme Aggregates," *Biotechnology and Bioengineering* 86(3):273-276, 2004.
Mateo et al., "Stabilisation of oxygen-labile nitrilases via co-aggregation with poly(ethyleneimine)," *Journal of Molecular Catalysis B: Enzymatic* 38:154-157, 2006.
Mateo et al., "Synthesis of enantiomerically pure (S)-mandelic acid using an oxynitrilase-nitrilase bienzymatic cascade: a nitrilase surprisingly shows nitrile hydratase activity," *Tetrahedron: Asymmetry* 17:320-323, 2006.
Schoevaart et al., "Preparation, Optimization, and Structures of Cross-Linked Enzyme Aggregates (CLEAs)," *Biotechnology and Bioengineering* 87(6);754-762, 2004.
Sheldon et al., "CLEAS: An effective technique for enzyme immobilization," *Specialty Chemicals Magazine*, pp. 40-42, Jul./Aug. 2003.
Sheldon et al., "Cross-linked enzyme aggregates (CLEAs): A novel and versatile method for enzyme immobilization (a review)," *Biocatalysis and Biotransformation* 23(3/4):141-147, 2005.
Sheldon et al., "Cross-linked enzyme aggregates (CLEAs)," *Methods in Biotechnology 22. Immobilization of enzymes an cells* ($2^{nd}$ ed.), Humana Press, Totowa, NJ, pp. 31-45, 2006.
Sheldon, "Immobilization of Enzymes as Cross-Linked Enzyme Aggregates: A Simple Method for Improving Performance," *Biocatalysis in the Pharmaceutical and Biotechnology Industries* , CRC Press, Taylor & Francis Group, Boca Raton, FL, pp. 351-362, 2006.
Sheldon et al., "Use of Cross-Linked Enzyme Aggregates (CLEAs) for performing biotransformations," *Chemistry Today* 25(1):62-67, 2007.
van Langen et al., "Penicillin Acylase Catalysed Synthesis of Ampicillin in Hydrophilic Organic Solvents," *Adv. Synth. Catal.*, 345:797-807, 2003.
van Langen et al., "Cross-Linked Aggregates of (R)-Oxynitrilase: A Stable, Recyclable Biocatalyst for Enantioselective Hydrocyanation," *Organic Letters* 7(2):327-329, 2005.
PCT Search Report, Mar. 23, 2007.
Herricks, et al., Direct fabrication of enzyme-carrying polyer nanofibers by electrospinning, Journal of Materials Chemistry, vol. 15, Jun. 30, 2005, pp. 3214-3245 (XP002423624).
Jia, et al.,Enzyme-Carrying Polymeric Nanofibers Prepared via Electrospinning for Use as Unique Biocatalysts, Biotechnol. Prog., 2002, 18, pp. 1027-1032.
Li, et al., Electrospinning of Polymeric and Ceramic Nanofibers as Uniaxially Aligned Arrays, Nano Lett., vol. 3, No. 8, 2003, pp. 1167-1171.
Yuris Dzenis, Spinning Continuous Fibers for Nanotechnology, Science, vol. 304, Jun. 25, 2004, pp. 1917-1919.
R. Schoevaart, et al., Preparation, Optimization, and Structures of Cross-Linked Enzyme Aggregates (CLEAs), Biotech and BioEng, vol 87, No. 6, 2004, pp. 754-762.

*Primary Examiner*—David M Naff
(74) *Attorney, Agent, or Firm*—James D. Matheson (57) ABSTRACT

The present invention relates generally to high stability, high activity biocatalytic materials and processes for using the same. The materials comprise enzyme aggregate coatings having high biocatalytic activity and stability useful in heterogeneous environment. These new materials provide a new biocatalytic immobilized enzyme system with applications in bioconversion, bioremediation, biosensors, and biofuel cells.

8 Claims, 5 Drawing Sheets

BIOCATALYTIC MATERIAL COMPRISING MULTILAYER ENZYME COATED FIBER

This invention was made with Government support under Contract DE-AC05-76RLO1830 awarded by the U.S. Department of Energy. The Government has certain rights in the invention.

FIELD OF THE INVENTION

The present invention relates generally to high stability, high activity biocatalytic materials and processes for using the same. The materials find application in such areas as biosensors, bioconversion, bioremediation, and biofuel cells.

BACKGROUND OF THE INVENTION

Enzymes are highly specific catalysts used increasingly for applications that include fine-chemical synthesis, pharmaceuticals, food processing, detergent applications, biosensors, bioremediation, protein digestion in proteomic analysis, and biofuel cells. Despite the variety of enzymes and methods available, development of both stable and active enzyme systems remains a challenging issue in realizing successful use of enzymes for many practical applications. Recent attention has focused on use of nanostructured materials including mesoporous media, nanoparticles, carbon nanotubes, and nanofibers as enzymatic supports, as such materials provide large surface areas that can lead to high volumetric enzyme activity. Nanofibers offer a number of attractive features compared with other nanostructures. First, nanofibers do not have the same mass transfer limitations of other nanostructures such as mesoporous media due to their reduced thicknesses. Second, nanofibers are easily formed or processed into various structures such as non-woven mats, well-aligned arrays, and/or membranes—all with controllable compositions and sizes. However, loading capacity by known methods is limited to monolayers. Accordingly, new processes are needed that can further improve enzyme loading leading to increased overall enzymatic activity.

SUMMARY OF THE INVENTION

A biocatalytic material is disclosed having high activity, high stability, and high enzyme loading capacity. The biocatalytic material includes one or more functional group(s) on the surface of the material covalently attached to one or more functional group(s) of a plurality of crosslinked enzymes and enzyme aggregates forming a biocatalytic coating on the material. The attachment between the functional group(s) on the surface and the functional group(s) of the enzymes and the enzyme aggregates provides substantial stability to the coating and the biocatalytic material. The activity and enzyme loading capacity of the biocatalytic material are greater than for a monolayer of enzymes.

In another aspect, a biocatalytic fiber(s) is/are disclosed having high activity, high stability, and high enzyme loading capacity. The biocatalytic fiber(s) has/have one or more reactive functional group(s) on the surface of the material that is/are covalently attached to one or more functional group(s) of a plurality of crosslinked enzymes and enzyme aggregates forming a biocatalytic coating on the fiber(s). The attachment between the functional group(s) on the surface and the functional group(s) of the enzymes and the enzyme aggregates provides substantial stability to the coating and the biocatalytic fiber(s). The activity and enzyme loading capacity of the biocatalytic fiber(s) is/are greater than for a monolayer of enzymes.

In an embodiment, carbonyl functional groups of the anhydride co-polymer molecule of the fibers provides for covalent attachment to functional groups of the enzymes and enzyme aggregates that are further cross-linked with a crosslinking reagent to other enzymes forming enzyme aggregates at the surface of the fibers.

In other embodiments, materials or fiber(s) is/are composed of at least one of polymers, co-polymers, glasses, inorganics, ceramics, composites, or combinations thereof.

In other embodiments, functional group(s) of the material, fibers, enzymes and/or enzyme aggregates comprise a member selected from di-aldehydes, glutaraldehyde [CAS No. 111-30-8]), aldehydes (—CHO), di-imides, di-isocyanates, isocyanates (—NCO), di-anhydrides, anhydrides, di-epoxides, epoxides, aminyl (—NH), sulfhydryl (—SH), carbonyl (—C=O), carboxyl (—COOH), alcohols (—OH), silyl, or combinations thereof.

In other embodiments, the enzyme aggregate coating of the biocatalytic materials or fiber(s) is a multilayer coating. Alternatively, the coating is two or more layers.

In other embodiments, fiber(s) is selected from nanofibers, microfibers, macrofibers, nanotubes, microtubes, macrotubes, or combinations thereof.

In other embodiments, the biocatalytic fibers have thicknesses of from about 5 nm to about 30,000 nm.

In other embodiments, the biocatalytic fibers have lengths greater than or equal to about 1,000 nm.

In various embodiments, crosslinking of the enzymes forming enzyme aggregates is achieved in conjunction with a crosslinking reagent.

In another embodiment, the coating of the materials or fiber(s) is substantially immobilized.

In other embodiments, attachment of the coating to the surface of the materials or fiber(s) is effected step-wise in conjunction with use of seed enzymes, wherein the seed enzymes further crosslink with enzyme aggregates forming the coating at the surface of the material or fiber(s).

In other embodiments, the attachment of the cross-linked enzyme aggregate coating of the materials or fiber(s) is directly effected by direct attachment to the one or more functional group(s) at the surface of the materials or fiber(s).

In an embodiment, the enzyme aggregate coated fiber(s) is/are used as biosensors or in a biosensor application or system.

In an embodiment, the enzyme aggregate coated materials or fiber(s) is/are used in a bioconversion process or application.

In an embodiment, the enzyme aggregate coated materials or fiber(s) is/are used in a bioremediation process or application.

In an embodiment, the enzyme aggregate coated materials or fiber(s) is/are used in a biofuel cell and/or in a biofuel cell process or system.

In an embodiment, the enzyme aggregate coated materials or fiber(s) is/are used in a detergent application or system.

In an embodiment, the enzyme aggregate coated materials or fiber(s) is/are used in a polymerase chain reaction process or system.

In another embodiment, the enzyme aggregate coated materials or fiber(s) is/are used in a biocatalytic process or system.

In another embodiment, the enzyme aggregate coated materials or fiber(s) is/are used in a protein digestion column or application.

In another embodiment, the enzyme aggregate coated materials or fiber(s) is/are used as a component of a lab-on-a-chip process or system.

In another embodiment, the enzyme aggregate coated materials or fiber(s) is/are used as a component of a proteomic analysis process or system.

TERMS

The term "seed" as used herein refers to the initial enzyme molecules that attach to the fiber substrates providing additional sites for attachment of additional enzymes and/or enzyme aggregates further loading such moieties to the polymer fibers.

The term "cross-linking" as used herein refers to the process of chemically joining two or more molecules by a covalent bond. Cross-linking reagents include, but are not limited to, homobifunctional and heterobifunctional reagents. Homobifunctional cross-linking reagents have two identical reactive functional groups available for binding, including, e.g., di-aldehydes, di-isocyanates, di-anhydrides, di-epoxides, di-imides (e.g., a carbodiimide reagent such as 1-ethyl-3-dimethyl aminopropylcarbodiimide (EDC), or the like. Heterobifunctional cross-linking reagents have two different reactive functional groups that allow, e.g., sequential step-wise conjugations. Heterobifunctional reactive groups include amine-reactive N-hydro-succinimide-esters (e.g., NHS or sulfo-NHS reagents) and sulfhydryl reactive groups, including, e.g., maleimides, pyridyl disulfides, and a-halo-acetyls. Reactive functional groups of either class of reagents may be photoreactive or thermoreactive. No limitations are intended. All cross-linking reagents capable of binding enzymes to the surface of a material are encompassed herein. Cross-linking reagents include, but are not limited to, e.g., di-aldehydes, glutaraldehyde [CAS No. 111-30-8]), aldehydes (—CHO), di-imides, 1-ethyl-3-dimethyl aminopropylcarbodiimide (EDC), di-isocyanates, isocyanates (—NCO), di-anhydrides, anhydrides, di-epoxides, epoxides, and reagents having functional groups selected from aminyl (—NH), sulfhydryl (—SH), carbonyl (—C=O), carboxyl (—COOH), alcohols (—OH), silyl (e.g., bis(trimethoxysilyl) hexane, or combinations thereof.

In general, reactive functional groups of the materials, fibers, and enzymes and enzyme aggregates disclosed herein include include, but are not limited to, e.g., di-aldehydes, aldehydes (—CHO), di-imides, di-isocyanates, isocyanates (—NCO), di-anhydrides, anhydrides, di-epoxides, epoxides, aminyl (—NH), sulfhydryl (—SH), carboxyl (—COOH), alcohols (—OH), silyl, or combinations thereof.

The term "coating" as used herein refers to a covering composed of enzymes and/or enzyme aggregates providing coverage at a level that is other than a monolayer.

The term "high loading" as used herein means enzymatic capacity or activity that is greater than that provided by a monolayer equivalent of enzymes.

The term "high activity" as used herein refers to enzymatic activity provided by the enzyme aggregate coating that is greater than activity provided by a monolayer equivalent of covalently attached enzymes.

The term "high stability" as used herein refers to an absence of measurable loss in enzyme activity observed under rigorous (>200 rpm) shaking conditions for at least a minimum of 100 days.

The term "substrate" as used herein in reference to enzyme-mediated reactions refers to a molecule or molecules undergoing reaction or that are reacting.

BRIEF DESCRIPTION OF THE DRAWINGS

A more complete appreciation of the invention will be readily obtained by reference to the following description of the accompanying drawing in which like numerals in different figures represent the same structures or elements.

DETAILED DESCRIPTION OF THE INVENTION

Disclosed herein are materials and fibers having enzyme-aggregate coatings and processes for using the same. The biocatalytic materials and fibers exhibit high-activity, high-stability, and high-enzyme loading capacity suitable for heterogeneous environments and applications. The term "fiber" as used herein refers to elongate, generally threadlike structures including, but not limited to, nanofibers, nanotubes, carbon nanotubes, microfibers, microtubes, macrofibers, macrotubes, or combinations thereof. Fibers selected for use have thicknesses in the range of from about 5 nm to about 30,000 nm, with lengths greater than or equal to about 1000 nm. Fibers may further comprise materials selected from, e.g., polymers, co-polymers, glasses, inorganics, ceramics, composites, or combinations thereof. However, the invention is not limited thereto. For example, enzyme-aggregate coatings may also be applied to, and/or utilized in conjunction with, other suitable materials selected from the same or different compound classes. In addition, such coatings may be equally applied and/or structurally attached to various surfaces of varying sizes and dimensions including, e.g., flat surfaces. Thus, no limitations are intended.

Figure 1:
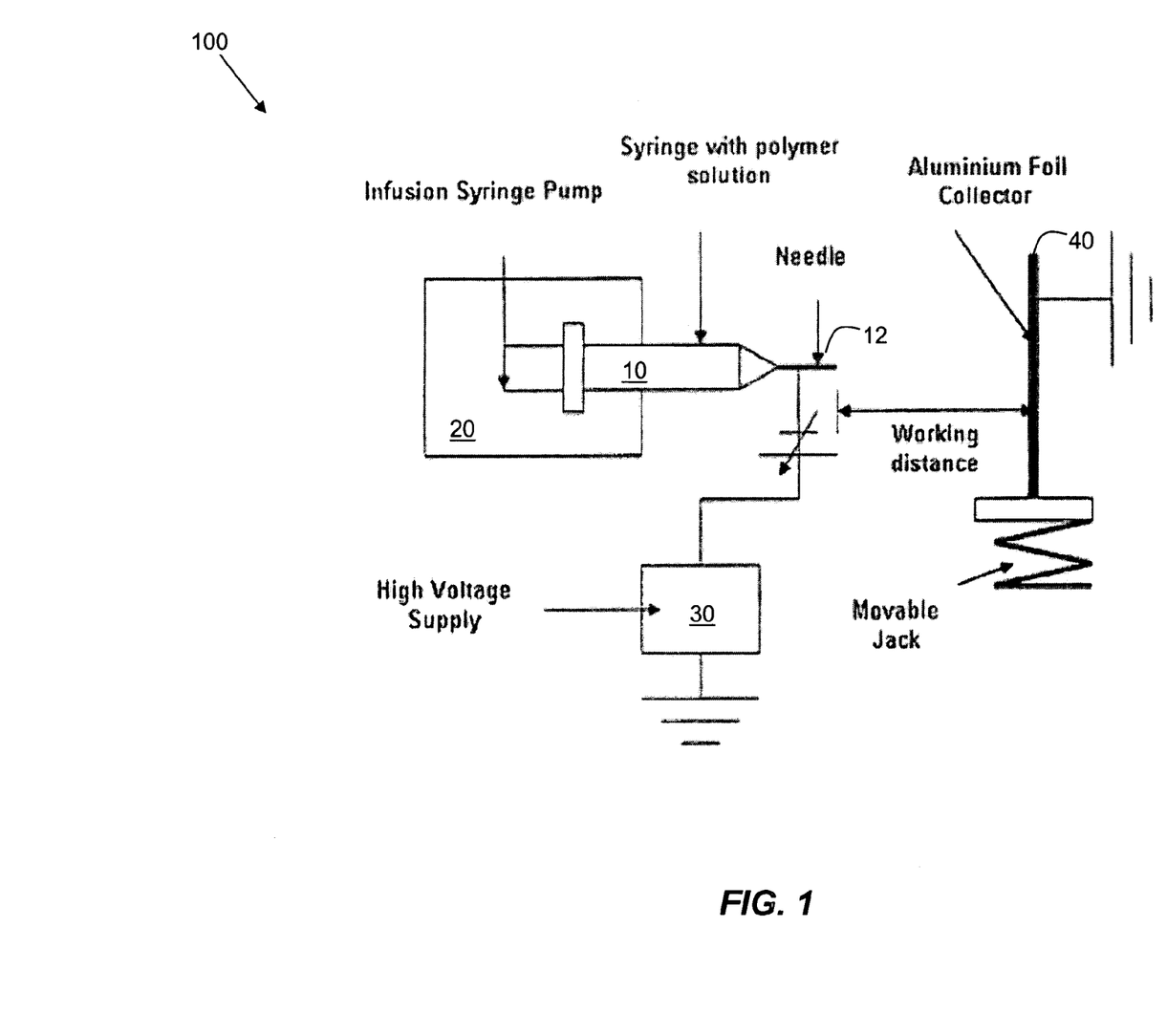
FIG. 1 illustrates an electrospinning apparatus for preparing nanoscale and microscale polymer fibers.

FIG. 1 illustrates a system 100 of a simple design for electrospinning (generating) polymer fibers suitable for use in conjunction with the invention, described further in Example 1 below, suitable for use in conjunction with the invention. System 100 includes a syringe 10 (e.g., 3 mL plastic, Becton-Dickinson, Franklin Lakes, N.J., USA) equipped with a 30-gauge stainless steel needle 12 (e.g., Precision-glide, Becton-Dickinson, Franklin Lakes, N.J., USA) for delivering a polymer solution. Polymer solution is delivered in conjunction with infusion pump 20 (e.g., a model PHD-2000 infusion pump, Holliston, Mass., USA). Rates are variable for delivery of polymer fluid. System 100 further comprises a high-voltage power supply 30 (e.g., a model ES30P-10W, Gamma High Voltage Research, Ormond Beach, Fla., USA) for applying a bias, e.g., of 7 kV, to needle 12. Electrospun fibers are collected on a clean (grounded) aluminum foil sheet 40 placed at a distance from the tip of needle 12 in the range from about 7 cm to about 10 cm, but are not limited thereto. No limitations are hereby intended. For example, as will be understood by those of skill in the art, system 100 may further comprise any of a number of additional components, vessels, and/or devices without limitation. For example, pressure and temperature of reactor 10 may be controlled in conjunction with programmable pressure and temperature controller(s) or other like devices and/or systems. In addition, systems and/or devices for pumping, transferring, spraying, delivering, mixing, pressurizing, heating, and/or storing fluids, reagents, and/or solvents may be used without limitation. In addition system 100 may incorporate devices for automated collection and handling of generated fibers without limitation. As will be appreciated by those of skill in the art, many and varied systems and processes may be employed for manufacture of both fibers and/or other materials upon which coatings described herein are attached. Thus, all processes and/or systems for preparing fibers and/or materials that will find application as substrates in conjunction with enzyme aggregate coatings are within the scope of the invention. No limitations are intended.

Figure 2:
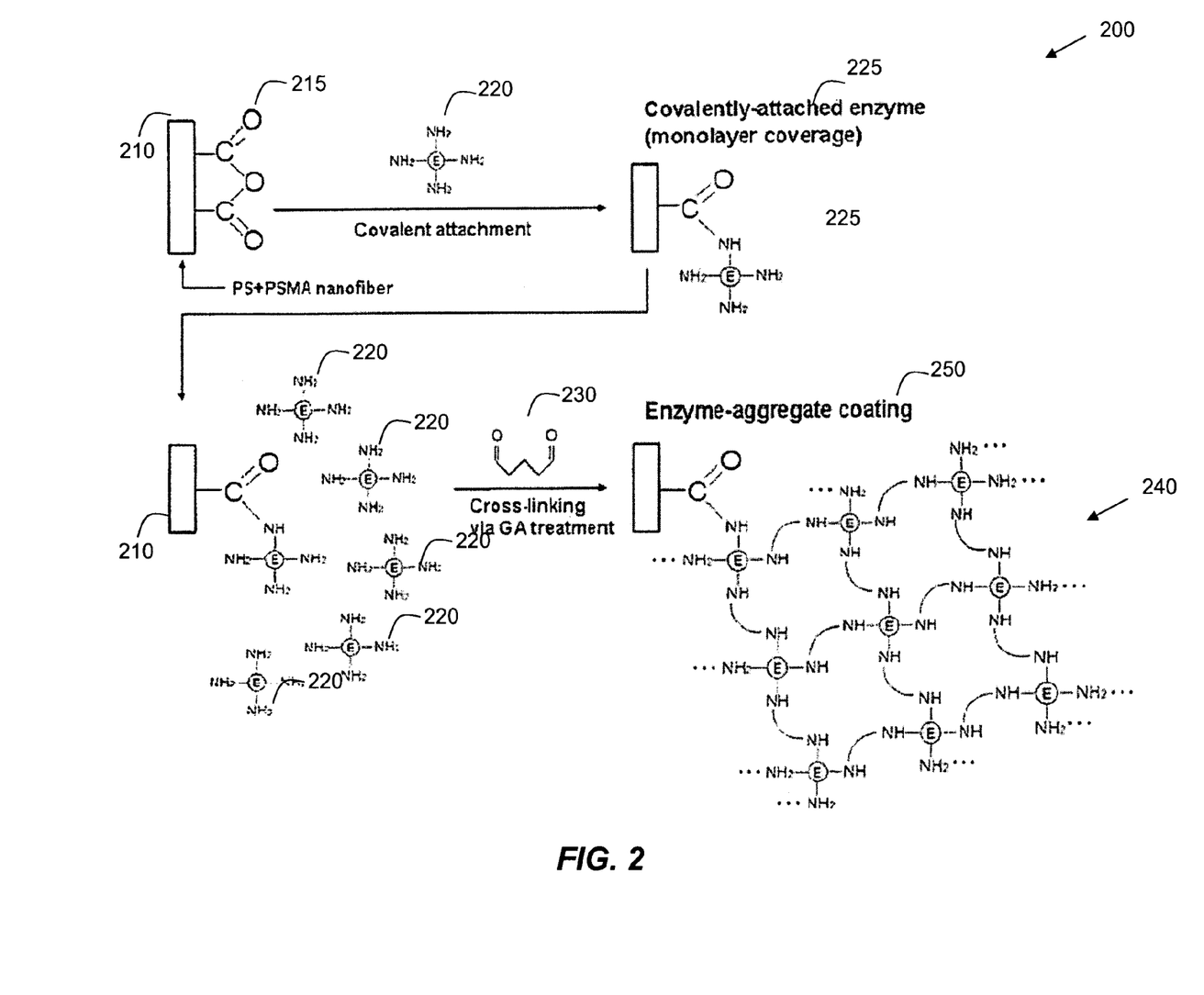
FIG. 2 illustrates preparation of high activity enzyme aggregate coatings for fibers, according to an embodiment of the invention.
Figure 3:
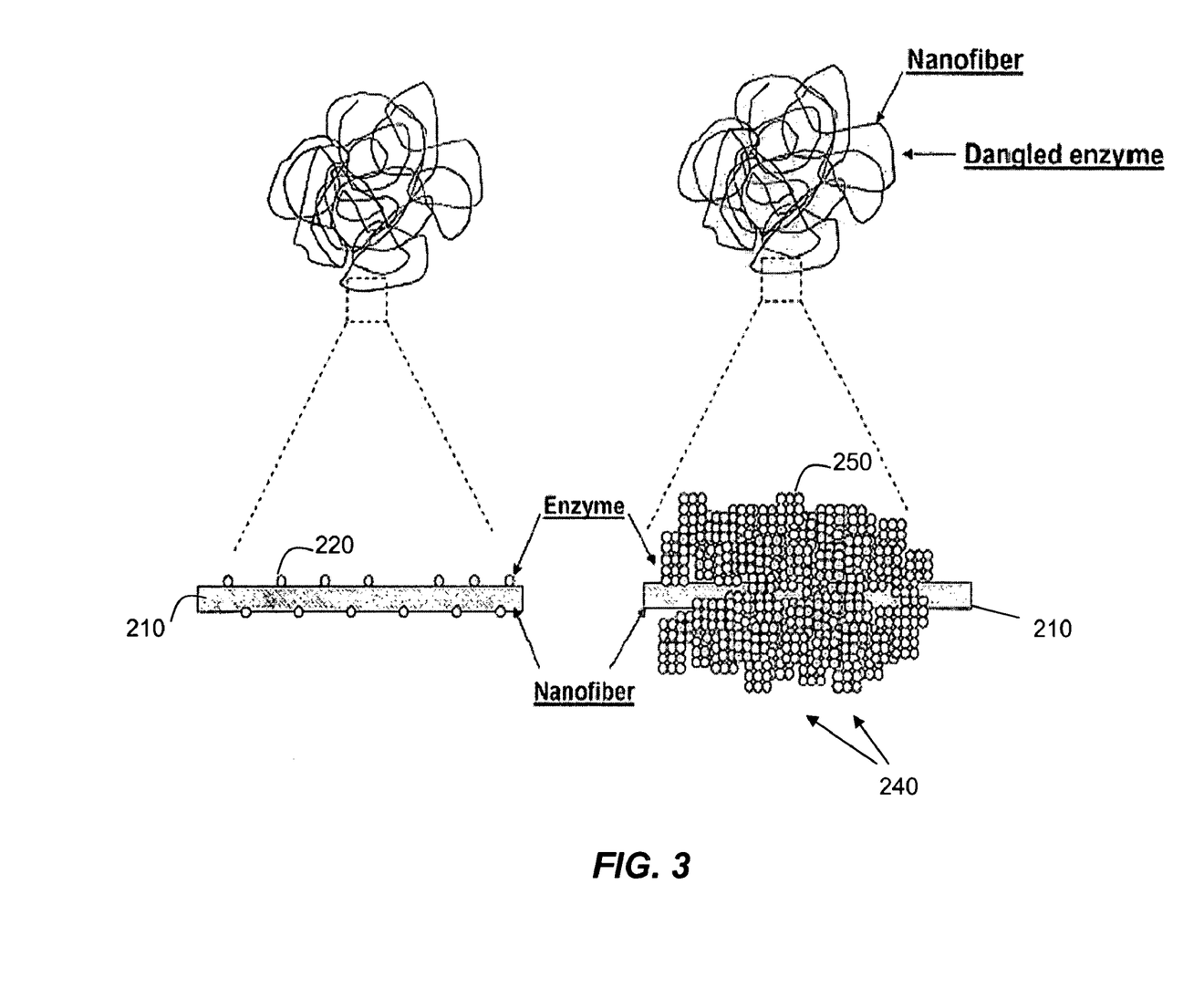
FIG. 3 illustrates preparation of high activity enzyme aggregate coatings for fibers involving use of "seed" enzymes, according to another embodiment of the invention

FIG. 2 illustrates a process 200 for preparation of high activity enzyme aggregate coatings and fibers. In the figure, a copolymer (PS and PSMA) fiber 210 is illustrated. Fiber 210 is coated with a coating 250 comprising highly crosslinked enzyme aggregates (CLEAs) 240 that are (e.g., covalently) attached to at least one functional groups 215 on the surface of fiber 210. Attachment of coating 250 to fiber 210 may be effected in a step-wise and/or in a batch-wise fashion. For example, as illustrated in FIG. 3, enzyme "seeds" 225 may attach to functional groups 215 at the surface of fiber 210 in a step-wise fashion. Subsequent treatment with linking agent 230, e.g., glutaraldehyde (GA) 230, in the presence of additional enzymes 220 crosslinks enzymes 220 to. "seed" enzymes 225 at the surface of fiber 210, covalently attaching them forming enzyme aggregates 240 from solution to the covalently attached seed enzyme molecules 225. The crosslinked enzymes 220 and/or enzyme aggregates 240 improve both the enzyme activity due to increased enzyme loading as well as the stability of the enzyme aggregate 240 coating 250. However, the process is not limited thereto.

In an alternate embodiment, enzymes 220 cross-linked as enzyme aggregates 240 in conjunction with linking agent 230 may be directly attached to functional groups 215 on the surface of fiber 210, bypassing need for a complex step involving attachment of "seed" enzymes 225. Thus, no limitations are intended.

The CLEAs 240 have high stability due to the highly crosslinked matrix of enzyme aggregates 240 providing high enzyme immobilization and high enzyme loading and thus high enzyme activity overall to fibers and/or materials to which aggregates 240 are attached, forming coating 250. High activity and high stability provide fiber 210 and/or other materials coated thereby with biocatalytic properties as they are biologically and/or catalytically active and useful in heterogeneous environments and systems.

The following examples are intended to promote a further understanding of the present invention. Example 1 describes preparation of PS and/or PS+PSMA nanofibers. Example 2 details the physical characterization of the polymer nanofibers. Example 3 details the nature of attachment of enzymes and/or enzyme aggregates to polymer fibers. Example 4 describes activity, leaching, and stability of α-Chymotrypsin (CT) immobilized fibers. Example 5 describes preparation and activity of enzyme (α-Chymotrypsin) immobilized aggregate coatings and fibers. Example 6 describes activity, leaching, and stability data of Trypsin (TR) immobilized fibers.

EXAMPLE 1

Preparation (Electrospinning) of Fibers using PS and/or PS+PSMA

Polymer fibers of polystyrene (PS) and/or poly(styrene co-maleic anhydride) (PSMA) were prepared from polymer solutions of polystyrene (PS) (MW=860,000) (Pressure Chemical Company, Pittsburgh, Pa., USA) or PS+PSMA prepared at room temperature by dissolving PS or a mixture of PS and poly(styrene-co-maleic anhydride) (PSMA) (MW=224,000; maleic anhydride content =7 wt %) (Aldrich, Milwaukee, Wis., USA) at a 2:1 weight ratio of PS:PSMA in tetrahydrofuran (THF) (HPLC, 99.9%) (Burdick and Jackson, Muskegon, Mich., USA), followed by magnetic stirring for 1-2 h. THF was used as the solvent due to its high vapour pressure, high volatility, and tendency to generate high pore densities. The concentration of PS and PSMA in the solutions was varied from 9 to 23 wt % and 5 to 9 wt % respectively, depending on the required size range of the fibers. As the concentration of the polymer (PS and/or PSMA) in the solvent increases, viscosity of the polymer solution increases, thus yielding thicker diameter fibers.

The polymer solution was loaded into a 3 mL plastic syringe (Becton-Dickinson, Franklin Lakes, N.J., USA) equipped with a 30-gauge stainless steel needle (Precision glide, Becton-Dickinson, Franklin Lakes, N.J., USA) made of stainless steel. A bias of 7 kV was applied to the needle using a high-voltage supply (ES30P-10W, Gamma High Voltage Research, Ormond Beach, Fla., USA). The solution was fed at a rate of 0.15 mL per hour using a syringe pump (PHD-2000 Infusion, Harvard Apparatus, Holliston, Mass., USA). The electrospun fibers were collected on clean aluminium foil (connected to the ground) placed at a suitable distance (7-10 cm) from the tip of the needle.

For this study, two different thickness fibers were synthesized-one less than 1 μm (e.g., nanofibers) and the other larger than 1 μm (e.g., microfibers), but is not limited thereto. Size of fibers (whether nanofibers or microfibers) is controlled by appropriate selection of concentrations for both PS and PSMA.

EXAMPLE 2

Physical Characterization of Electrospun PS or PS+PSMA Nanofibers

Electrospun polymer nanofiber and microfiber specimens were analyzed with scanning electron microscopy (SEM) and reflection-absorption infrared spectroscopy (RAIRS).

For SEM, a thin layer of gold (~10 nm) is coated to prevent charging. Image characterization was done using a PhilipsXL-20SEM (Philips ElectronOptics, Eindhoven, the Netherlands). For RAIRS, the e-spun fibers were collected on a glass slide. The RAIRS analysis was performed using a NEXUS 670 infrared spectrometer (ThermoNicolet, Wis., USA). Incident and reflection angles for the IR beam were 82°; spectral resolution was 4 $cm^{-1}$.

The detailed size distribution were obtained with statistical analysis of fibers imaged with SEM. The fiber diameter of the thin one is 444±106 nm and that of the thick one is 3.04±1.03. Hereafter, the former will be called nanofibers and the latter will be called microfibers. Nanosize fibers are of primary interest for enzyme immobilization studies.

In addition to the size distribution, SEM analysis revealed a few notable features. First, nano-sized fibers sometimes show formation of beads along the fibers while micro-sized fibers are almost bead-free. Results may be related to Taylor-cone instability during the electrospinning process, as described e.g., by Huang et al., *Compos. Sci. Technol* 63, pp. 2223-53. The process was adjusted to minimize bead formation on nanofibers and the samples used for enzyme immobilization were largely bead free. Second, high resolution SEM images show that the surface texture of electrospun fibers contains small holes. The typical size of surface holes is about 100-400 nm. Formation of holes on the surface of the electrospun fibers is often observed especially when a high vapor pressure solvent is used. On the nanofibers, 'holes' exist as depressions whose diameters are similar to the diameter of the fiber, and are sufficiently common that the fibers have a somewhat irregular shape.

EXAMPLE 3

Attachment of Enzymes and/or Enzyme Aggregates to Polymer Fibers

The PSMA copolymer is an illustrative copolymer for generating nanoscale and microscale fibers described herein given that the copolymer contains a maleic anhydride (MA) functional group that readily forms covalent bonds with primary amines of enzyme molecules. As illustrated in FIG. 2.

The approach using copolymers such as PSMA can be used with any other polymer fibers if the maleic anhydride group is intact and exposed at the fiber surface.

RAIRS spectra showed presence of maleic anhydride (MA) groups in the electrospun fibers. In particular, the IR spectrum of the PS nanofiber sample showed all the characteristic bands of polystyrene: a C—H stretch of the aromatic ring at 3000-3100 $cm^{-1}$, aromatic C—H deformation of the aromatic ring at 1450 and 1490 $cm^{-1}$, a C=C stretch in the aromatic ring at 1605 $cm^{-1}$, and aromatic overtones over the range from 1700-2000 $cm^{-1}$. The IR spectrum of the PS+PSMA fiber exhibits additional peaks representing the anhydride group: an asymmetric (as) C=O stretch at 1860 $cm^{-1}$ and symmetric (sym) C=O stretch at 1780 $cm^{-1}$.

EXAMPLE 4

Activity, Leaching, and Stability of α-Chymotrypsin (CT)-immobilized fibers

α-Chymotrypsin (CT) accelerates cleavage (e.g., via hydrolysis) of peptide bonds linking one amino acid to another amino acid in a polypeptide chain. CT was used as an illustrative enzyme to test catalytic stability and activity of the enzyme in enzyme-immobilized fibers.

Activity of CT-immobilized nanofibers was assessed in conjunction with absorption measurements at 410 nm of a reaction product (p-nitroaniline) resulting from enzymatic action (i.e., hydrolysis) of a substrate protein material, N-succinyl-Ala-Ala-Pro-Phe p-nitroaniline (TP) in an aqueous buffer solution (10 mM sodium phosphate buffer, pH 7.8) under rigorous shaking (200 rpm) conditions. Activity data were calculated from the slope of the 410 nm absorption line as a function of time, normalized to the total weight of nanofibers used.

Leaching of CT was also monitored by measuring the protein contents of the aqueous buffer solution (10 mM sodium phosphate, pH 7.8) under shaking condition (200 rpm) at each time point. Leached CT was measured by absorption measurement at 280 nm.

Stability (catalytic) was also investigated as a function of time by continuous incubation of the nanofiber samples in the same aqueous buffer (10 mM sodium phosphate, pH 7.8) under rigorous shaking (200 rpm) conditions. At each time point, the residual activity was measured, and the relative activity was calculated from the ratio of residual activity to initial activity. After each activity measurement, samples were extensively washed with fresh buffer to remove all residual amounts of substrate and product from the sample.

Table 1 provides initial data collected over a 2-day period for catalytic activity and leaching. for CT covalently attached to polymer fibers compared to CT adsorbed to polymer fibers, respectively. Stability data are presented in FIG. 4.

TABLE 1

Activity and leaching data for α-chymotrypsin (CT) adsorbed and covalently attached to polymer (PS and PS + PSMA) fibers, respectively.

| | Adsorbed CT on PS fibers | | | Covalently Attached CT on PS + PSMA fibers | |
|---|---|---|---|---|---|
| | Activity (μM/min/mg)[a] | Leached Enzyme in Buffer (μg)[b] | | Activity (μM/min/mg)[a] | Leached Enzyme in Buffer (μg)[b] |
| Day 0 | 0.051 | N.A.[c] | Day 0 | 0.098 | N.A.[c] |
| Day 1 | 0.008 | 3.8 | Day 1 | 0.023 | 3.2 |
| Day 2 | 0.005 | 1.0 | Day 2 | 0.014 | N.D.[d] |

[a] Activity was measured by the hydrolysis of TP (N-succinyl-Ala-Ala-Pro-Phe p-nitroaniline) in an aqueous buffer (10 mM sodium phosphate, pH 7.8) and normalized to the total weight of nanofibers.
[b] Leached quantity of CT was measured by absorbance at 280 nm after a one day incubation in a shaking condition (200 rpm).
[c] N.A. = Not Applicable. Excessive washings were performed right after each CT immobilization until no leached CT was observed in the washing solution within a limited time span (for about one hour).
[d] N.D. = Not Detectable. After 30 days incubation, neither CT activity nor CT leaching could be observed with adsorbed and covalently attached CT samples.

Figure 4:
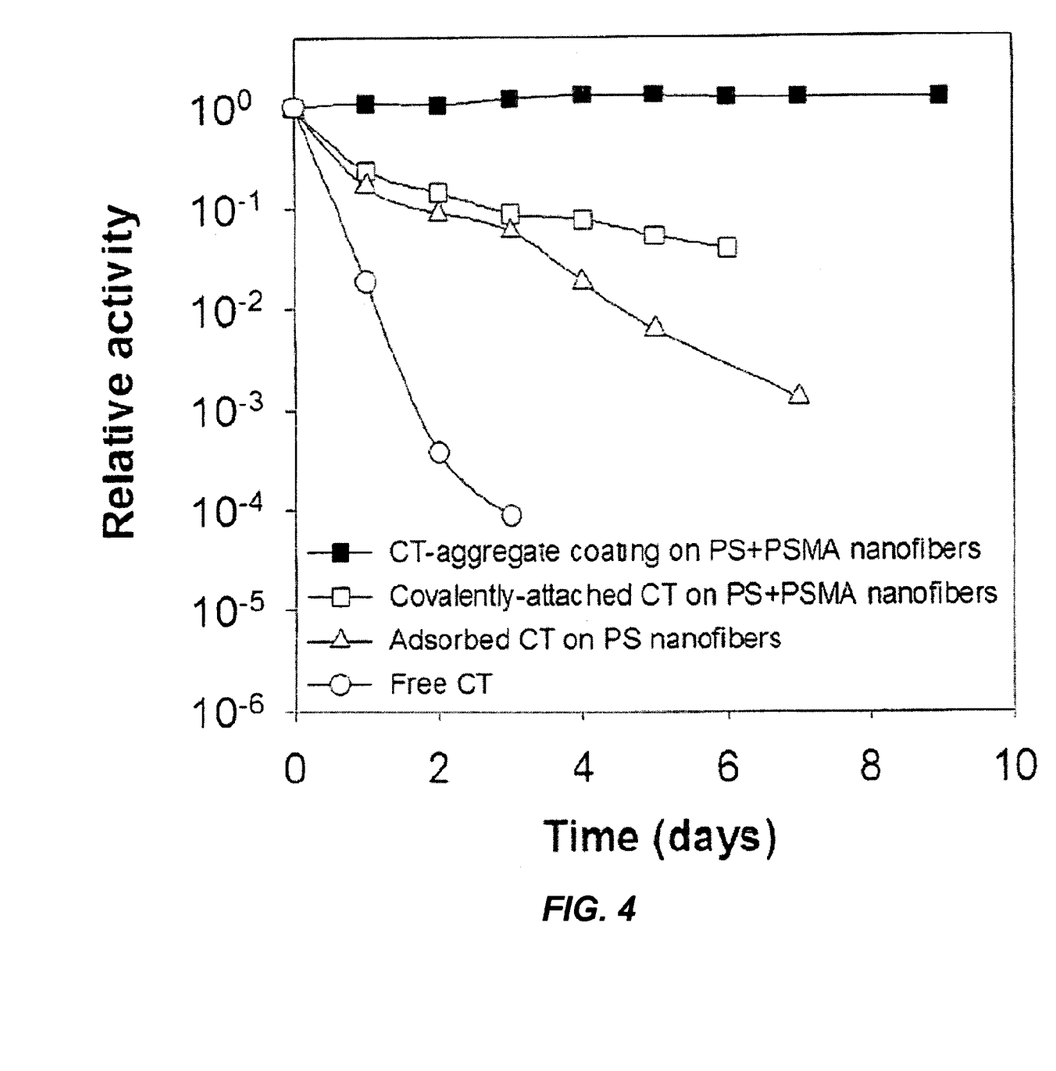
FIG. 4 is a plot showing stabilities (as measured by relative activities in an aqueous buffer solution shaking at 200 rpm) for free α-chymotrypsin (CT), adsorbed CT, covalently attached CT, and CT-aggregate coatings on nanofibers as a function of time.

Table 1 shows the initial activity of PS+PSMA nanofibers with covalently attached CT was 1.9 times greater (0.098 vs. 0.051 μM/min/mg) than that of PS nanofibers with adsorbed CT. Leaching was presumed to be a result of fibers initially being coated with both covalently attached and adsorbed CT molecules. During the first day of incubation in a shaking condition, fibers with covalently attached CT and those with adsorbed CT both showed significant leaching of CT. After day 2 of incubation, no further leaching of CT molecules was detected from fibers with covalently attached CT, while PS fibers with absorbed CT continued to leach additional CT. FIG. 4 shows that after the first few days (when both fibers leach CT), fibers with covalently attached CT exhibited greater stability and activity. Results suggest that covalent attachment to surface-available anhydride groups occurred. FIG. 4 also shows the activity of free CT in solution for comparison. The activity of free CT rapidly decreased due to autolysis (half-life of 5 h) while the adsorbed and covalently attached CT showed a marginal improvement of enzyme stability with half-lives of 18 and 35 h, respectively based on all data points collected (including those during which initial leaching of adsorbed enzyme from the covalently attached preparation was presumed to be occurring). Results indicate some improvement in activity and stability of CT is achieved when covalently attached covalently to PS+PSMA polymer fibers as compared to adsorption on PS fibers.

EXAMPLE 5

Preparation and Activity of Enzyme (α-Chymotrypsin) Immobilized Aggregate Coatings and Fibers Enzyme activity is important for successful applications involving enzymes in a variety of heterogeneous immobilization systems. Although covalent attachment provides some improvement in enzyme (e.g., CT) activity and stability of fibers compared to adsorbed CT, results were not expected to be sufficient to maintain high enzyme activity indefinitely under rigorous shaking conditions (200 rpm) due to enzyme denaturation. To develop a more stable and active enzyme system, polymer nanofibers and microfibers comprising enzyme-aggregate coatings were fabricated as described hereinafter.

PS+PSMA fibers were prepared as described in Example 1. PS+PSMA nanofibers were incubated in glass vials containing 1 mL of 10 mM phosphate buffer (pH 7.8) and 20 mg α-chymotrypsin (CT) (Sigma, St Louis, Mo., USA). Vials were shaken at 200 rpm at room temperature for 30 minutes, and then moved to a refrigerator for additional rocking at 30 rpm. Following a 90-minute incubation at 4° C., glutaraldehyde (GA) Sigma (St Louis, Mo.) solution was added to a final GA concentration of about 0.5% w/v, and the mixture was rocked (on a rocker plate) at 30 rpm at 4° C. overnight. The enzyme-aggregate-coated nanofibers were transferred to new glass vials, and washed with 100 mM phosphate buffer (pH 7.8) and 100 mM Tris-HCl (pH 7.8). To cap unreacted aidehyde groups, nanofibers were incubated in Tris-HCl buffer for 30 minutes. After capping, nanofibers were washed extensively with 10 mM phosphate buffer (pH 7.8) until no enzymes were detected in the washing solution (~five washings). The enzyme-aggregate-coated nanofibers were stored in 10 mM phosphate buffer (pH 7.8) at 4 volts DC. Two control samples were also prepared for comparison with enzyme-aggregate-coated nanofibers, (i) a first with covalently attached CT on nanofibers, prepared by omitting the GA treatment step, and (ii) a second prepared using simple adsorption of CT without covalent linkages between CT and polymer nanofibers, prepared using PS nanofibers instead of PS+PSMA nanofibers.

Activity of the CT-immobilized nanofiber coatings was determined as described in Example 4 using absorption measurements of the reaction product (p-nitroaniline) resulting from enzymatic action (i.e., hydrolysis) of N-succinyl-Ala-Ala-Pro-Phe p-nitroaniline (TP) in aqueous buffer (10 mM sodium phosphate, pH 7.8). ~1 mg of coated (biocatalytic) fibers were transferred into new glass vials, and 4.04 ml of 10 mM phosphate buffer (pH 7.8) containing 40 µl of TP (at a concentration of 10 mg mL$^1$ in N,N-dimethylformamide (DMF) (Sigma, St Louis, Mo.) was added to initiate the enzymatic reaction. Vials were shaken at 200 rpm and aliquots were removed in a time-dependent fashion. The p-nitroaniline product of enzymatic catalysis in each aliquot was measured by the absorbance at 410 nm (A410) and activity was calculated from the slope of the A410 line with time. Samples were washed a minimum of three times after each activity measurement with 10 mM phosphate buffer solution (pH 7.8) to remove residual amounts of (TP) substrate and (p-nitroaniline) catalysis product from each sample. Leaching of CT was also monitored by measuring protein contents of the aqueous buffer solution at each time point. At each time point, residual activity was measured, and relative activity was calculated as the ratio of residual activity to initial activity. Table 2 compares initial enzyme activities for nanoscale (<1 µm) and microscale (>1 µm) fibers.

TABLE 2

Initial activity measured for nanoscale (<1 µm) and microscale (>1 µm) polymer (PS + PSMA) fibers.

| Sample | Description | Initial Activity (µM/min)/mg fibers [a] |
|---|---|---|
| 1 | Covalently attached CT on PS + PSMA fibers (<1 µm) | 0.098 |
| 2 | Covalently attached CT on PS + PSMA (>1 µm) | 0.076 |
| 3 | CT-aggregate coating on PS + PSMA (<1 µm) | 0.868 |
| 4 | CT-aggregate coating on PS + PSMA (>1 µm) | 0.633 |

[a] Activity was measured by hydrolysis of N-succinyl-Ala-Ala-Pro-Phe-p-nitro aniline in an aqueous buffer (10 mM sodium phosphate, pH 7.8) and normalized to the total weight of polymer fibers.

Results for samples 1 and 2 represent, at best, activity associated with at most a monolayer of CT coverage, as insufficient quantity of enzymes was available to form aggregate coatings. Results 3 and 4 in Table 2 compare aggregate coating results for microscale and nanoscale fibers, respectively. Activity (per mg) measured for covalently attached CT on microfibers was 78% of that of nanofibers. The activity (per mg) of CT-aggregate-coated microfibers (>1 µm) was 73% of the activity with CT-aggregate-coated nanofibers (>1 µm). In addition, activity of CT-aggregate-coated nanofibers was eight times higher than the initial activity of nanofibers with only covalently attached CT. This substantial improvement of CT activity with CT-aggregate-coated nanofibers can be explained by the much higher enzyme loading effected at the surface of the fiber. No leaching of enzymes was detected from CT-aggregate-coated nanofibers from the beginning of incubation under shaking conditions. FIG. 4 shows the stability of CT-aggregate-coated nanofibers over a period of 9 days (shaking conditions as usual).

Essentially no loss of activity was measured over a period in excess of 33 days under rigorous shaking conditions. The extended stability and catalytic activity observed for the enzyme-aggregate-coated fibers under a shaking condition indicates the covalent attachment of enzyme aggregates on the external surfaces of the fibers creates a new immobilized enzyme system effective in stabilizing the enzyme activity. In particular, the (enzyme) stability of CT-aggregate-coated nanofibers is greatly improved over that of either monolayer-coated fibers or that of the free (unattached) CT,. The stability of the CT-aggregate coating showed negligible loss of CT activity for a period of more than 1 month (data to 33 days were collected). Further, insufficient loss of activity was measured in which to estimate or calculate a half life for the experiment. This dramatic stabilization of CT in the immobilized aggregate coating can be explained by several factors, including absence of CT leaching and good stability of cross-linked enzyme aggregates (CLEAs) themselves. It is also noteworthy that enzyme aggregation prevented the autolysis of CT molecules.

Catalytic stability of the coated fibers was also determined by continuous incubation of fiber samples in the same aqueous buffer (10 mM phosphate buffer, pH 7.8) under rigorous shaking (200 rpm) conditions. Table 3 presents results for catalytic activity over a 4 day period for nanofibers (NF) treated with and without linking agent glutaraldehyde (GA) following adsorption with α-chymotrypsin (CT), i.e., NF-CT-GA, as compared to those adsorbed with α-chymotrypsin alone, i.e., NF—CT.

TABLE 3

Activity measured for nanofibers treated with and without glutaraldehyde following adsorption with α-chymotrypsin.

| Samples | Treatment Δ | Activity @Time t = 0 (days) * | Activity @Time t = 4 (days) * |
|---|---|---|---|
| 1 | NF-CT-GA | $6.720 \times 10^{-1}$ | $6.659 \times 10^{-1}$ |
| 2 | NF-CT | $1.758 \times 10^{-3}$ | $4.853 \times 10^{-4}$ |

* Units of activity: (μM/min)/mg; activity was divided by fiber weight (mg).
Δ NF-CT-GA: glutaraldehyde (GA) treated nanofibers (NF) following adsorption with α-chymotrypsin (CT); NF-CT: nanofibers adsorbed with CT only.

Table 3 shows negligible loss of activity for the nanofibers treated with glutaraldehyde following adsorption with α-chymotrypsin (i.e., NF-CT-GA) as compared to the nanofibers adsorbed with α-chymotrypsin alone, (i.e., NF—CT). FIG. 4 shows relative activities over a longer time period, i.e., upwards of 9 days. The initial activity of PS+PSMA nanofibers with covalently attached CT was 1.9 times higher than that of PS nanofibers with adsorbed CT (Table 1). It is presumed that the fibers are initially coated with both covalently attached and adsorbed CT molecules. During the first day of incubation in a shaking condition, fibers with covalently attached CT and those with adsorbed CT both showed significant CT leaching. No more leaching of CT molecules was detected after 2-day incubation from nanofibers with covalently attached CT while PS nanofibers with absorbed CT leached more CT. As seen in the figure, after the first few days (when both fibers leach CT), fibers with covalently attached CT exhibit greater stability of the activity. By comparison, activity of free CT rapidly decreased due to autolysis (half-life of 5 h) while the adsorbed and covalently attached CT showed a marginal improvement of enzyme stability with half-lives of 18 and 35 h, respectively, based on all data points (including those during which initial leaching of adsorbed enzyme from the covalently attached preparation is presumed to occur). Results suggest activity stability is promoted by covalent attachment to surface-available anhydride groups.

To check the role of covalently attached seed enzyme molecules in the fabrication of CT-aggregate coating, we prepared the PS nanofibers by electrospinning a PS solution without addition of PSMA copolymer. Then, we adsorbed CT on the PS nanofibers and treated them with 0.5% GA solution, which is exactly the same as the fabrication process of CT-aggregate coating on the PS+PSMA nanofibers. The final nanofibers would consist of PS nanofibers and enzyme aggregates without any covalent linkages between them. This sample exhibited a serious leaching of enzymes and the quantity of leached CT was 4.6 μg after 1 day incubation. It was observed that white powders of enzyme aggregates separated from PS nanofibers and leached into a buffer solution. The activity of this control sample continuously decreased in a shaking condition, and the relative activity was 85% after 2 day incubation. The calculated half-life of this control was 11.5 days, much shorter than that of CT-aggregate-coated PS+PSMA nanofibers. Results suggest the covalently attached enzymes play a significant role in developing a stable form of enzyme aggregate coating on the surface of the fibers.

The availability of the anhydride group was again supported by stabilities of the PS+PSMA nanofibers with covalently attached CT or covalently attached CT aggregates, compared to PS fibers with only adsorbed CT or PS fibers treated to produce enzyme aggregates, as described hereinabove.

EXAMPLE 6

Figure 5:
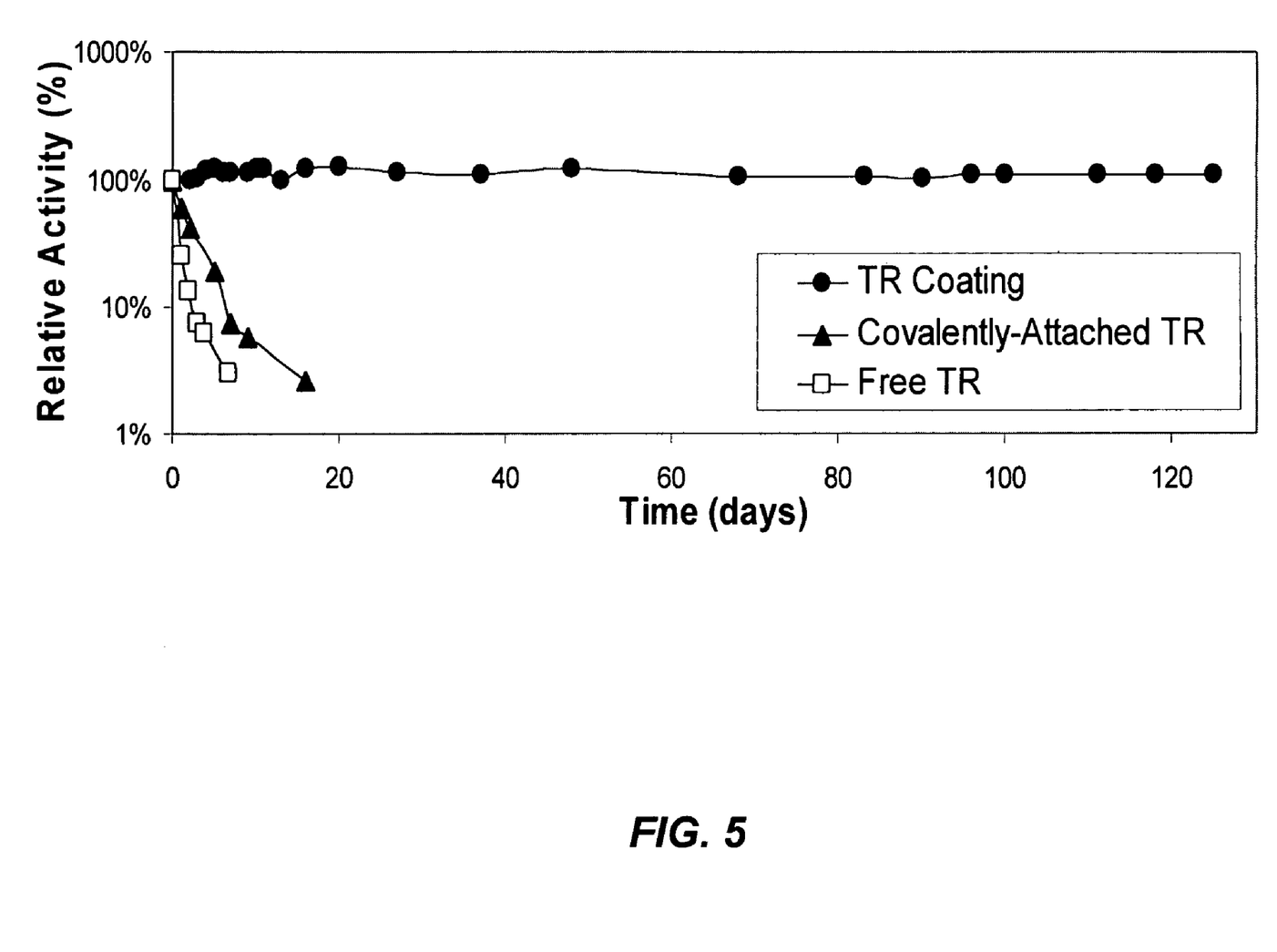
FIG. 5 is a plot showing stability of a trypsin-aggregate coating (i.e., NF-T-GA) covalently bound to polystyrene (PS) and polystyrene-maleic anhydride (PSMA) co-polymer fibers, the stability measured as a function of time compared to free trypsin (TR).

Activity and Stability of Enzyme (Trypsin) Immobilized Aggregate Coatings and Fibers Fibers were prepared as described in Example 1 and coated as described in Example 4 with aggregates of trypsin (TR), an alternate enzyme and tested as described herein. Stabilities of free TR, adsorbed TR, covalently attached TR, and TR-aggregate coating on fibers in an aqueous buffer solution (10 mM sodium phosphate, pH 7.8) under a shaking condition (200 rpm). Relative activity was again calculated from the ratio of residual activity at each time point to initial activity. FIG. 5 presents stability data for the TR-aggregate coating, and also shows activity of free TR and covalently attached TR in solution for comparison. Data presented in FIG. 5 show negligible loss of TR activity over a period of up to about 120 days. Activity loss was sufficiently low as to calculate an estimate for half life for the TR-aggregate coated fibers. This dramatic stabilization and immobilization of TR as a coating of TR-enzyme aggregates on the fibers can be explained by several factors, including, but not limited to, e.g., no leaching of TR enzyme, and cross-linked enzyme aggregates (CLEAs). Enzyme aggregation also prevents autolysis of TR enzymes from the fibers. Half life of covalently-attached TR was 2.2 days (0.8 days in another batch of preparation). The half-life of the TR coating on fibers could not be measured since there was no inactivation even after 118 days of incubation under shaking conditions.

CONCLUSIONS

Fibers and/or materials providing a large surface area for the attachment of enzymes and/or enzyme aggregates are ideal substrates for immobilizing enzymes and can provide high enzyme activity, stability, and loading capacity to the fibers and/or materials. A unique approach for fabricating enzyme-aggregate coatings on surfaces of fibers has been described. These enzyme-aggregate-coated fibers and coatings also exhibit extended stability of the catalytic activity under a shaking condition indicating that covalent attachment of enzyme aggregates on external surfaces of fibers and/or materials creates a new immobilized enzyme system effective in stabilizing the enzyme activity. These aggregate coatings have been demonstrated to improve not only the enzyme activity but also the enzyme stability when applied to fibers of various sizes. These active and stable fiber mats were highly durable and could be easily recovered from a solution even after more than 1-month incubation in a rigorous shaking condition. This new approach of enzyme coating on nanofibers, yielding high activity and stability, creates a useful new biocatalytic immobilized enzyme system with potential applications in bioconversion, bioremediation, and biosensors.

While the preferred embodiments of the present invention have been shown and described, it will be apparent to those skilled in the art that many changes and modifications may be made without departing from the invention in its true scope and broader aspects. The appended claims are therefore intended to cover all such changes and modifications as fall within the spirit and scope of the invention.

We claim:

1. A biocatalytic material, comprising:
   a preformed fiber having an external surface with a plurality of preselected enzymes attached thereto, each of said plurality of preselected enzymes is covalently attached to a functional group of said fiber that secures said plurality of preselected enzymes to said surface;
   said plurality of covalently attached preselected enzymes are further covalently attached to aggregates of crosslinked enzymes; and
   said aggregates of crosslinked enzymes provide a multilayer enzyme coating on said surface of said fiber that provides an enzyme activity greater than a monolayer of said preselected enzymes.

2. The biocatalytic material of claim 1, wherein said fiber is selected from the group consisting of: polymer fibers, co-polymer fibers, glass fibers, inorganic fibers, ceramic fibers, composite fibers, and combinations thereof.

3. The biocatalytic material of claim 2, wherein said fiber has a thickness of from about 5 nm to about 30,000 nm.

4. The biocatalytic material of claim 2, wherein said fiber has a thickness greater than or equal to about 20 nm.

5. The biocatalytic material of claim 2, wherein said fiber has a length greater than or equal to about 1,000 nm.

6. The biocatalytic material of claim 1, wherein said enzyme activity has a longevity of greater than 100 days without measurable loss in activity.

7. The biocatalytic material of claim 1, wherein said functional groups are selected from the group consisting of: an aminyl (—NH), a sulfhydryl (—SH), an alcohol (—OH), a carbonyl (=C=O), a carboxyl (—COOH), an aldehyde (—CHO), an isocyanate (—NCO), an anhydride, an epoxide, a silyl, and combinations thereof.

8. The biocatalytic material of claim 1, wherein said aggregates of crosslinked enzymes are covalently attached to said preselected enzymes with a cross-linking reagent selected from the group consisting of: a di-isocyanate, a di-anhydride, a di-epoxide, a di-aldehyde, a di-imide, 1-ethyl-3-dimethyl aminopropylcarbodiimide, and combinations thereof.

* * * * *